(12) United States Patent
Berger et al.

(10) Patent No.: US 7,780,671 B2
(45) Date of Patent: Aug. 24, 2010

(54) BONE RESECTION APPARATUS AND METHOD FOR KNEE SURGERY

(75) Inventors: Richard A. Berger, Chicago, IL (US); Adam H. Sanford, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 477 days.

(21) Appl. No.: 11/337,283

(22) Filed: Jan. 23, 2006

(65) Prior Publication Data

US 2007/0173854 A1 Jul. 26, 2007

(51) Int. Cl.
*A61B 17/58* (2006.01)
*A61B 17/60* (2006.01)

(52) U.S. Cl. ............................. 606/88; 606/79

(58) Field of Classification Search .......... 606/79, 606/82, 86 R, 87, 88
See application file for complete search history.

(56) References Cited

U.S. PATENT DOCUMENTS

| | | | |
|---|---|---|---|
| 2,697,433 A | 12/1954 | Zehnder | |
| 3,532,088 A | 10/1970 | Fiore | |
| 4,349,018 A | 9/1982 | Chambers | |
| 4,457,307 A | 7/1984 | Stillwell | |
| 4,524,766 A * | 6/1985 | Petersen | 606/88 |
| 4,566,448 A | 1/1986 | Rohr, Jr. | |
| 4,567,886 A | 2/1986 | Petersen | |
| 4,574,794 A | 3/1986 | Cooke et al. | |
| 4,646,729 A | 3/1987 | Kenna et al. | |
| 4,738,253 A | 4/1988 | Buechel et al. | |
| 4,759,350 A | 7/1988 | Dunn et al. | |
| 4,825,857 A * | 5/1989 | Kenna | 606/88 |
| 4,841,975 A | 6/1989 | Woolson | |
| 4,938,762 A | 7/1990 | Wehrli | |
| 4,952,213 A | 8/1990 | Bowman et al. | |
| 5,002,547 A | 3/1991 | Poggie et al. | |
| 5,007,936 A | 4/1991 | Woolson | |
| 5,116,338 A | 5/1992 | Walker et al. | |
| 5,122,144 A | 6/1992 | Bert | |
| 5,213,112 A | 5/1993 | Niwa et al. | |
| 5,230,338 A | 7/1993 | Allen et al. | |
| 5,234,433 A | 8/1993 | Bert | |
| 5,251,127 A | 10/1993 | Raab | |
| 5,275,603 A | 1/1994 | Ferrante et al. | |

(Continued)

FOREIGN PATENT DOCUMENTS

DE 20202615 U1 6/2002

(Continued)

OTHER PUBLICATIONS

Wright Medical Technology, Inc., Advance® Unicompartmental Knee System, Product Brochure MK638-102. © 2002.
Wright Medical Technology, Inc., Advance® Unicompartmental Knee System, Product Brochure MK151-603 Rev. 02-04, © 2003.

*Primary Examiner*—Eduardo C Robert
*Assistant Examiner*—Ellen C Hammond
(74) *Attorney, Agent, or Firm*—Baker & Daniels LLP (57) ABSTRACT

A bone resection apparatus and its method of use for knee surgery are presented. In one aspect of the invention, the apparatus includes a spacer and a tibial cut guide. The spacer has a first surface engageable with the cut distal femoral bone and a second surface opposite the first surface engageable with the uncut proximal tibial bone in joint articulating relationship. The spacer further includes a cut guide support. The tibial cut guide has a cutter guide defining a cut plane and a support engaging element engageable with the cut guide support. The cut guide support and support engaging element cooperate to position the cut plane in relative to the first surface.

15 Claims, 8 Drawing Sheets

U.S. PATENT DOCUMENTS

| | | | |
|---|---|---|---|
| 5,305,203 A | 4/1994 | Raab | |
| 5,306,276 A | 4/1994 | Johnson et al. | |
| 5,342,367 A | 8/1994 | Ferrante et al. | |
| 5,342,368 A | 8/1994 | Petersen | |
| 5,344,423 A | 9/1994 | Dietz et al. | |
| 5,364,401 A | 11/1994 | Ferrante et al. | |
| 5,364,402 A | 11/1994 | Mumme et al. | |
| 5,368,552 A | 11/1994 | Williamson et al. | |
| 5,445,640 A | 8/1995 | Johnson et al. | |
| 5,451,228 A | 9/1995 | Johnson et al. | |
| 5,458,645 A | 10/1995 | Bertin | |
| 5,474,559 A | 12/1995 | Bertin et al. | |
| 5,484,446 A | 1/1996 | Burke et al. | |
| 5,486,180 A | 1/1996 | Dietz et al. | |
| 5,514,139 A | 5/1996 | Goldstein et al. | |
| 5,514,143 A | 5/1996 | Bonutti et al. | |
| 5,527,316 A | 6/1996 | Stone et al. | |
| 5,540,696 A | 7/1996 | Booth et al. | |
| 5,551,429 A | 9/1996 | Fitzpatrick et al. | |
| 5,562,674 A | 10/1996 | Stalcup et al. | |
| 5,593,411 A | 1/1997 | Stalcup et al. | |
| 5,597,379 A | 1/1997 | Haines et al. | |
| 5,601,563 A | 2/1997 | Burke et al. | |
| 5,611,802 A | 3/1997 | Samuelson et al. | |
| 5,628,750 A | 5/1997 | Whitlock et al. | |
| 5,643,272 A | 7/1997 | Haines | |
| 5,649,928 A | 7/1997 | Grundei | |
| 5,681,316 A | 10/1997 | DeOrio et al. | |
| 5,681,320 A | 10/1997 | McGuire | |
| 5,682,886 A | 11/1997 | Delp et al. | |
| 5,683,397 A | 11/1997 | Vendrely et al. | |
| 5,688,280 A | 11/1997 | Booth, Jr. | |
| 5,704,941 A | 1/1998 | Jacober et al. | |
| 5,743,915 A | 4/1998 | Bertin et al. | |
| 5,755,803 A | 5/1998 | Haines et al. | |
| 5,776,201 A * | 7/1998 | Colleran et al. | 623/20.15 |
| 5,788,700 A | 8/1998 | Morawa et al. | |
| 5,800,438 A | 9/1998 | Tuke et al. | |
| 5,810,824 A | 9/1998 | Chan | |
| 5,824,085 A | 10/1998 | Sahay et al. | |
| 5,860,980 A * | 1/1999 | Axelson et al. | 606/88 |
| 5,871,018 A | 2/1999 | Delp et al. | |
| 5,879,354 A | 3/1999 | Haines et al. | |
| 5,904,691 A | 5/1999 | Barnett et al. | |
| 5,911,723 A | 6/1999 | Ashby et al. | |
| 5,921,992 A | 7/1999 | Costales et al. | |
| 5,935,128 A * | 8/1999 | Carter et al. | 606/86 B |
| 5,995,738 A | 11/1999 | DiGioia, III et al. | |
| 6,002,859 A | 12/1999 | DiGioia, III et al. | |
| 6,033,415 A | 3/2000 | Mittelstadt et al. | |
| 6,051,016 A | 4/2000 | Mesaros et al. | |
| 6,056,754 A | 5/2000 | Haines et al. | |
| 6,077,270 A | 6/2000 | Katz | |
| 6,090,114 A | 7/2000 | Matsuno et al. | |
| 6,167,145 A | 12/2000 | Foley et al. | |
| 6,197,064 B1 | 3/2001 | Haines et al. | |
| 6,267,762 B1 | 7/2001 | Millard et al. | |
| 6,285,902 B1 | 9/2001 | Kienzle, III et al. | |
| 6,296,646 B1 | 10/2001 | Williamson | 606/90 |
| D457,957 S * | 5/2002 | Sanford et al. | D24/140 |
| 6,396,939 B1 | 5/2002 | Hu et al. | |
| 6,402,762 B2 | 6/2002 | Hunter et al. | |
| 6,430,434 B1 | 8/2002 | Mittelstadt | |
| 6,450,978 B1 | 9/2002 | Brosseau et al. | |
| 6,475,228 B1 | 11/2002 | Mesaros et al. | |
| 6,477,400 B1 | 11/2002 | Barrick | |
| 6,478,799 B1 * | 11/2002 | Williamson | 606/90 |
| 6,490,467 B1 | 12/2002 | Bucholz et al. | |
| 6,503,254 B2 | 1/2003 | Masini | |
| 6,514,259 B2 | 2/2003 | Picard et al. | |
| 6,551,325 B2 | 4/2003 | Neubauer et al. | |
| 6,554,837 B1 | 4/2003 | Hauri et al. | |
| 6,575,980 B1 | 6/2003 | Robie et al. | |
| 6,595,997 B2 | 7/2003 | Axelson, Jr. et al. | |
| 6,632,225 B2 * | 10/2003 | Sanford et al. | 606/87 |
| 6,685,711 B2 | 2/2004 | Axelson, Jr. et al. | |
| 6,695,848 B2 | 2/2004 | Haines | |
| 6,712,824 B2 | 3/2004 | Millard et al. | |
| 6,859,661 B2 | 2/2005 | Tuke | |
| 6,932,823 B2 | 8/2005 | Grimm et al. | |
| 7,029,477 B2 | 4/2006 | Grimm | |
| 7,060,074 B2 * | 6/2006 | Rosa et al. | 606/88 |
| 7,094,241 B2 | 8/2006 | Hodorek et al. | |
| 7,201,755 B2 | 4/2007 | Faoro | |
| 7,235,080 B2 | 6/2007 | Hodorek | |
| 7,335,206 B2 | 2/2008 | Steffensmeier et al. | |
| 7,371,240 B2 * | 5/2008 | Pinczewski et al. | 606/88 |
| 2002/0068942 A1 | 6/2002 | Neubauer et al. | |
| 2002/0133160 A1 | 9/2002 | Axelson, Jr. et al. | |
| 2002/0133162 A1 | 9/2002 | Axelson, Jr. et al. | |
| 2002/0133163 A1 | 9/2002 | Axelson, Jr. et al. | |
| 2002/0133164 A1 | 9/2002 | Williamson | 606/90 |
| 2002/0198530 A1 | 12/2002 | Sanford | |
| 2003/0069585 A1 | 4/2003 | Axelson, Jr. et al. | |
| 2003/0069591 A1 | 4/2003 | Carson et al. | |
| 2003/0100906 A1 | 5/2003 | Rosa et al. | |
| 2003/0216741 A1 | 11/2003 | Sanford | 606/87 |
| 2003/0225413 A1 | 12/2003 | Sanford et al. | |
| 2003/0233149 A1 | 12/2003 | Hodorek | |
| 2004/0039396 A1 | 2/2004 | Couture et al. | |
| 2004/0102785 A1 | 5/2004 | Hodorek | 606/87 |
| 2004/0122305 A1 | 6/2004 | Grimm et al. | |
| 2004/0152955 A1 | 8/2004 | McGinley et al. | |
| 2004/0153062 A1 | 8/2004 | McGinley et al. | |
| 2004/0249386 A1 * | 12/2004 | Faoro | 606/88 |
| 2004/0249387 A1 | 12/2004 | Faoro | |
| 2005/0070910 A1 | 3/2005 | Keene | |
| 2005/0143746 A1 | 6/2005 | Steffensmeier et al. | |
| 2005/0182415 A1 | 8/2005 | Steffensmeier et al. | |
| 2005/0203528 A1 | 9/2005 | Couture et al. | |
| 2005/0203541 A1 | 9/2005 | Steffensmeier et al. | |
| 2006/0030855 A1 | 2/2006 | Haines | |
| 2006/0036257 A1 | 2/2006 | Steffensmeier et al. | |
| 2006/0149276 A1 | 7/2006 | Grimm | |
| 2006/0173463 A1 * | 8/2006 | Dees, Jr. | 606/88 |
| 2006/0189998 A1 * | 8/2006 | Rasmussen | 606/88 |
| 2006/0195111 A1 | 8/2006 | Couture | |
| 2006/0217734 A1 | 9/2006 | Sanford et al. | |
| 2006/0235421 A1 * | 10/2006 | Rosa et al. | 606/88 |
| 2006/0247647 A1 | 11/2006 | Hodorek et al. | |

FOREIGN PATENT DOCUMENTS

| | | |
|---|---|---|
| DE | 20303498 U1 | 7/2003 |
| EP | 0104732 A1 | 4/1984 |
| EP | 2648699 A1 | 12/1990 |
| EP | 00709061 A1 | 5/1996 |
| EP | 00809969 B1 | 10/2002 |
| EP | 0839501 B1 | 3/2003 |
| EP | 1579812 A1 | 9/2005 |
| EP | 1424042 B1 | 3/2007 |
| FR | 2679766 A1 | 2/1993 |
| FR | 2732581 A1 * | 10/1996 |
| FR | 2776176 A1 | 9/1999 |
| FR | 2819168 A1 | 7/2002 |
| WO | WO01/66021 A1 | 9/2001 |
| WO | WO01/85038 A1 | 11/2001 |
| WO | WO2004/017842 A2 | 3/2004 |
| WO | WO2004/019792 A1 | 3/2004 |

* cited by examiner

BONE RESECTION APPARATUS AND METHOD FOR KNEE SURGERY

FIELD OF THE INVENTION

The invention relates to a bone resection apparatus and method for knee surgery. In particular, the invention relates to an apparatus for spacing and resecting a tibial bone during knee replacement surgery.

BACKGROUND

Degenerative and traumatic damage to the articular cartilage of the knee joint can result in pain and restricted motion. Knee replacement surgery is frequently utilized to alleviate the pain and restore joint function. An incision is made into the knee joint to expose the bones comprising the joint. Cutting guides are used to guide the removal of the articular surfaces that are to be replaced. Artificial joint components are positioned to replace the resected bone ends in order to establish the desired alignment and mechanics of the joint. In a total knee replacement, all of the articulating compartments of the joint are repaired with prosthetic components. However, often only one compartment of the knee joint, typically the medial compartment, is impaired. Thus, in a unicondylar knee replacement, only the damaged compartment is repaired with prosthetic bearing components.

Figure 1:
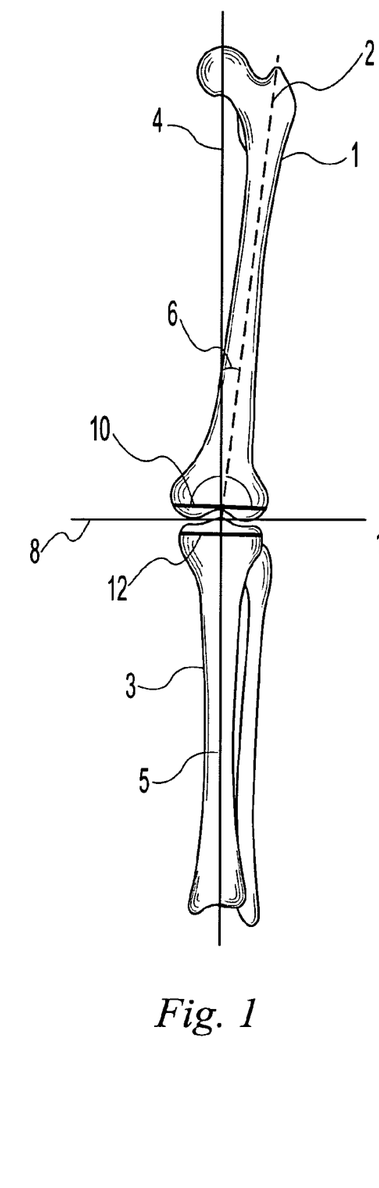
FIG. 1 is a front elevation view of a tibia and a femur showing axes of the knee joint.
Figure 2:
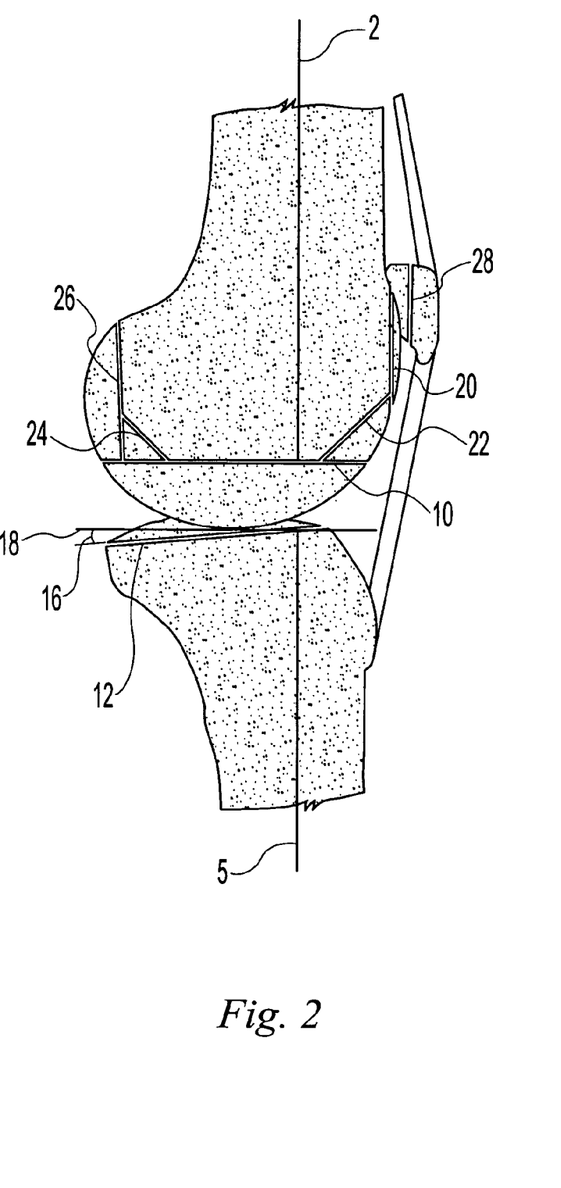
FIG. 2 is a side section view of a knee joint showing typical bone cuts used in replacing the joint surfaces.
Figure 3:
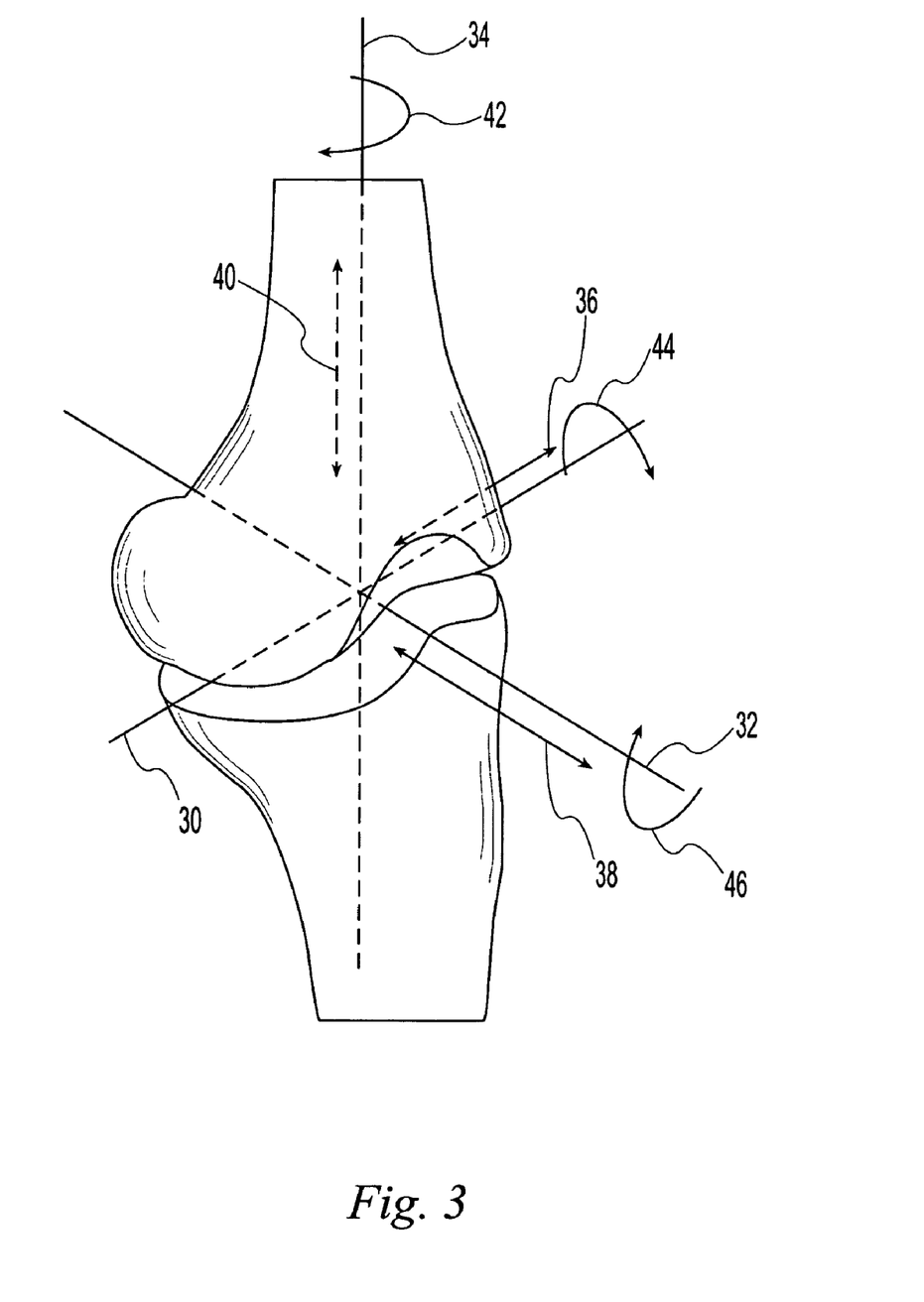
FIG. 3 is a perspective view of knee joint showing aspects of component positioning.

FIGS. 1-3 illustrate several aspects of implant orientation. FIG. 1 illustrates various axes of the lower limb in the frontal plane. Axes can be defined for each segment of the lower limb. For example, the femur 1 has an anatomic axis 2 coinciding generally with its intramedullary canal. It also has a mechanical axis 4, or load axis, running from the center of the femoral head to the center of the knee. The angle 6 between these two axes 2, 4 in the frontal plane varies within the patient population but is on the order of 4-9°. The two axes 2, 4 are approximately superimposed in the sagittal plane (FIG. 2). Likewise, the tibia 3 has a mechanical axis 5 coinciding generally with its intramedullary canal. The mechanical axis 5 of the tibia runs from the center of the knee to the center of the ankle. The transverse axis, or joint line 8, about which the knee flexes, is parallel to a line through the medial and lateral femoral condyles and parallel to the tibial plateau. Typically, the distal femur and proximal tibia are resected to be parallel to the joint line 8, and thus perpendicular to the mechanical axes 4, 5 as indicated at 10 and 12. The intersection of the femoral and tibial mechanical axes 4, 5 may subtend a small angle relative to one another. However, the angle is small such that the axes 4,5 are approximately collinear and may be treated as collinear for most purposes.

FIG. 2 illustrates the knee joint from the side or sagittal view and various bone cuts that may be made to align implant components. The distal femoral cut 10 is typically made perpendicular to the femoral axes 2, 4 in the sagittal plane. The proximal tibial resection 12 is typically cut to match the natural posterior slope, or rotation, 16 of the proximal tibia relative to the mechanical axes 4, 5. The amount of posterior slope 16 relative to a reference line 18 perpendicular to the mechanical axes 4, 5 varies in the patient population but is on the order of 7°. The distance between the distal femoral cut 10 and proximal tibial cut 12 along the mechanical axes 4, 5 is the extension gap. Other cuts may be made depending on the components that are to be implanted. These include an anterior femoral cut 20, anterior femoral chamfer cut 22, posterior femoral chamfer cut 24, and posterior femoral cut 26. The patella 7 may also be cut 28 to allow for replacement of the patellar articular surface. In a unicondylar knee replacement, only the medial or lateral side of the knee joint is resurfaced. Furthermore, the trochlear, or patellar bearing, surface of the femur is typically left intact in a unicondylar procedure. Unicondylar implant designs vary, but typically only the distal femoral cut 10, posterior femoral chamfer cut 24, and posterior femoral cut 26 are needed to accommodate the unicondylar femoral implant.

FIG. 3 depicts six aspects of component positioning relative to a coordinate system in which the x-axis 30 corresponds approximately to the joint line 8, the z-axis 34 corresponds approximately to the mechanical axes 4 and 5, and the y-axis 32 is normal to the other two. Position along each of these axes is depicted by arrows. Position along the x, y, and z axes determines the medial/lateral (dx) 36, anterior/posterior (dy) 38, and proximal/distal (dz) 40 positioning of components respectively. Rotation about each of these axes is also depicted by arrows. Rotation about the z-axis (rz) 42 corresponds anatomically to external rotation of the femoral component, rotation about the x-axis (rx) 44 corresponds to extension plane rotation, and rotation about the y-axis (ry) 46 corresponds to varus/valgus rotation.

SUMMARY

The present invention provides a bone resection apparatus and method for knee surgery.

In one aspect of the invention, the apparatus includes a spacer and a tibial cut guide. The spacer has a first surface engageable with the cut distal femoral bone and a second surface opposite the first surface engageable with the uncut proximal tibial bone in joint articulating relationship. The spacer further includes a cut guide support. The tibial cut guide has a cutter guide defining a cut plane and a support engaging element engageable with the cut guide support. The cut guide support and support engaging element cooperate to position the cut plane in predetermined posterior slope angular relationship to the first surface.

In another aspect of the invention, the apparatus includes an implant, a spacer, and a tibial cut guide. The implant has a femoral component thickness, a tibial component thickness, and an overall implant thickness which is the sum of the femoral component thickness, the tibial component thickness, and an additional joint laxity distance corresponding to a desired amount of joint laxity. The spacer has a body including a planar seating surface, an arcuate condylar surface arching away from the seating surface generally in the shape of an anatomic femoral condyle, and an elongated support having a longitudinal axis. The spacer has a spacer thickness normal to the planar seating surface. The tibial cut guide has a body with a front surface, a back surface, and an aperture through the body from the front surface to the back surface having a longitudinal axis. The aperture is engageable with the support for linear translation parallel to the aperture longitudinal axis. A cutter guide slot extends through the body from the front surface to the back surface. The cutter guide slot defines a cut plane oriented parallel to the aperture longitudinal axis. The cut plane is spaced a predetermined distance from the aperture such that with the aperture engaged with the support the cut plane is spaced from the arcuate condylar surface a tibial resection distance.

In another aspect of the invention, a method of performing knee surgery includes: resecting a portion of the distal femoral bone; inserting a spacer into the knee joint to abut the cut surface of the femoral bone, the spacer having an arcuate condylar portion facing away from the cut surface; abutting the arcuate condylar portion with the proximal tibial surface; mounting a tibial cut guide on the spacer to position a cut plane at a predetermined posterior slope angle and depth relative to the cut surface of the femoral bone; and guiding a cutter in the cut plane with the cut guide to form a planar surface on the tibia.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Embodiments of the present invention include a spacer sized and shaped to temporarily replace a resected femoral condyle to permit normal articulation of the knee joint intraoperatively. The spacer includes a seating portion for seating on the cut surface of the bone and a condylar portion arching away from the seating portion generally in the shape of an anatomic femoral condyle. The seating portion may engage the bone surface in a simple frictional engagement. The seating portion may include a roughened surface, barbs, spikes, pins, and/or other fixation enhancement features to fix it in position on the bone surface. Separate fasteners such as pins, screws, clips, clamps, and/or other fasteners may also be used to fix the spacer in position. Separate fasteners may engage surfaces, grooves, slots, holes and/or other features of the spacer to hold it in position. For example, the seating portion may include a flat surface frictionally engageable with the cut surface of the femur. The condylar portion of the spacer may be curved in the sagittal plane to match the anterior/posterior curvature of the femoral condyle. The condylar portion may be curved in the frontal plane to match the medial/lateral curvature of the femoral condyle. The spacer may be provided in a variety of sizes and curvatures to permit selection of a spacer that best matches the patient's anatomy. For example, the spacer may be provided in a variety of sizes to permit selection of a spacer that blends smoothly with the resected femur anteriorly, posteriorly, medially, and laterally to permit a gapless, or approximately gapless, fit to the bone and smooth anatomic articulation of the knee joint. The spacer may have a condylar thickness parallel to the mechanical axis of the femur. The spacer may be provided in different condylar thicknesses to permit selection of a spacer thickness to replace the same thickness of bone that was resected to restore pre-surgical kinematics. The spacer thickness may also be chosen to be larger or smaller than the bone removed to correct a varus or valgus abnormality of the pre-surgical knee.

The spacer may include a cut guide support. The support may include a hole, slot, groove, rail, beam, stem, handle, and/or other structure for supporting a cut guide relative to the spacer. The support may form a predetermined angle relative to the seating portion to position the cut guide at a predetermined angle relative to the seating portion in the sagittal plane. For example the support may incorporate a predetermined posterior slope angle relative to the seating portion. The spacer may be provided in different versions with different posterior slope angles. For example, the posterior slope angle may vary from zero degrees to ten degrees. For example, versions may be provided with three degrees, five degrees, and seven degrees of posterior slope. The cut guide support may engage the cut guide to permit varus/valgus rotation of the cut guide relative to the seating portion in the frontal plane. For example, the cut guide support may have a circular cross section to permit varus/valgus rotation of the cut guide about the support axis. The support may engage the cut guide to restrain the cut guide from rotating relative to the support. For example, the support may have a non-circular cross section to rotationally constrain the cut guide with respect to varus/valgus rotation. For example, the support may have a "T"-shaped, "D"-shaped, "I"-shaped, and/or other non-circularly shaped cross section. For example, the support may include a "T"-shaped stem projecting away from the support at an angle to the seating portion.

A tibial cut guide for use with the spacer may include a body having a support engaging element and a cutter guide. The support engaging element may be positionable at various positions along the support to allow the distance between the cut guide and the bone to be adjusted. The support engaging element may include a hole, slot, groove, rail, beam, stem, handle, and/or other structure for engaging the support. For example, where the support includes a stem extending away from the spacer, the support engaging element may include a complimentary shaped aperture through the cut guide body. The cut guide may be slidable along the support to position the cut guide adjacent to the tibia. The cutter guide may include a planar surface, slot, rail, and/or other suitable cutter guide defining a cut plane and able to guide a saw blade, burr, mill, and/or other suitable cutter within the cut plane. For example, the cutter guide may include a slot defining a cut plane. The slot may receive a saw blade and constrain the saw blade to motion within the cut plane to produce a planar surface on the tibia. The cut plane defined by the slot may be oriented parallel to the support engaging element in the sagittal plane such that adjustment of the cut guide along the support does not change the cut plane location relative to the tibia.

The cut guide may further include a fixation element to accommodate attaching the cut guide to the tibia. The fixation element may include a roughened surface, barbs, spikes, pins, and/or other fixation enhancement features to fix the cut guide in position on the tibia. Separate fasteners such as pins, screws, clips, clamps, and/or other fasteners may also be used to fix the cut guide in position. Separate fasteners may engage the bone and surfaces, grooves, slots, holes and/or other features of the cut guide to hold it in position. For example, the cut guide may include fixation holes for receiving pins to attach the cut guide to the tibia. The fixation element may be oriented parallel to the cut plane and support engaging element so that the cut guide may be removed and repositioned easily on the bone. For example, where the fixation element includes holes for receiving pins, the holes may be parallel to the cut plane and support engaging element so that the cut guide can be slipped off of the pins and support, the knee repositioned, e.g. from extension to flexion, and the cut guide slipped back onto the pins. For example, this may be advantageous where it is desirable to set the cut guide with the knee in extension but where it may be safer or more convenient to cut the tibia with the knee in flexion.

Figure 4:
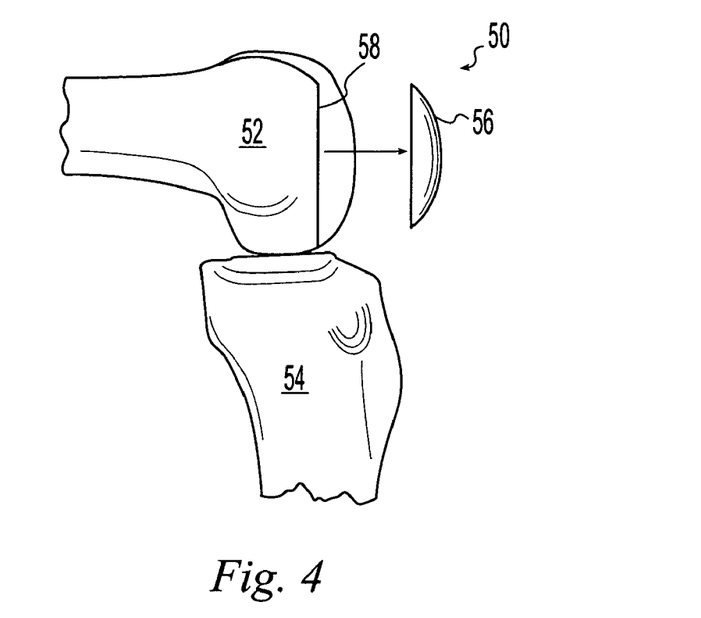
FIG. 4 is a side elevation view of a knee joint with a distal condyle resected according to the present invention.
Figure 5:
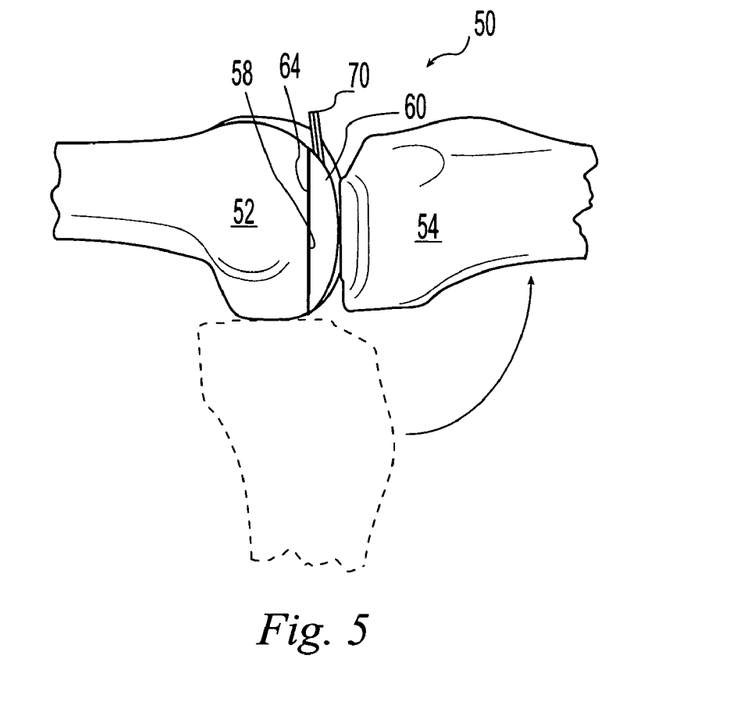
FIG. 5 is a side elevation view of the knee joint of FIG. 4 showing a spacer according to the present invention and the knee being articulated into extension.
Figure 6:
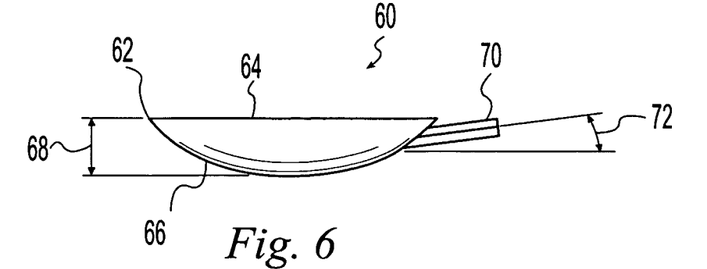
FIG. 6 is a side elevation view of the spacer of FIG. 5.
Figure 7:
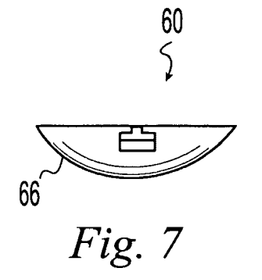
FIG. 7 is a front elevation view of the spacer of FIG. 5.
Figure 8:
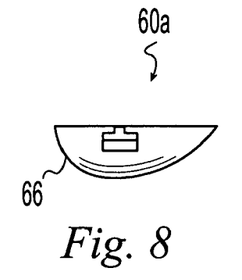
FIGS. 8-9 are front elevation views of an alternative anatomically shaped spacers.
Figure 9:
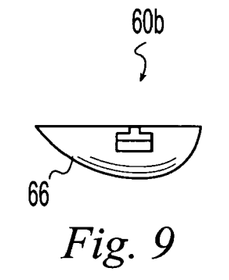
Figure 11:
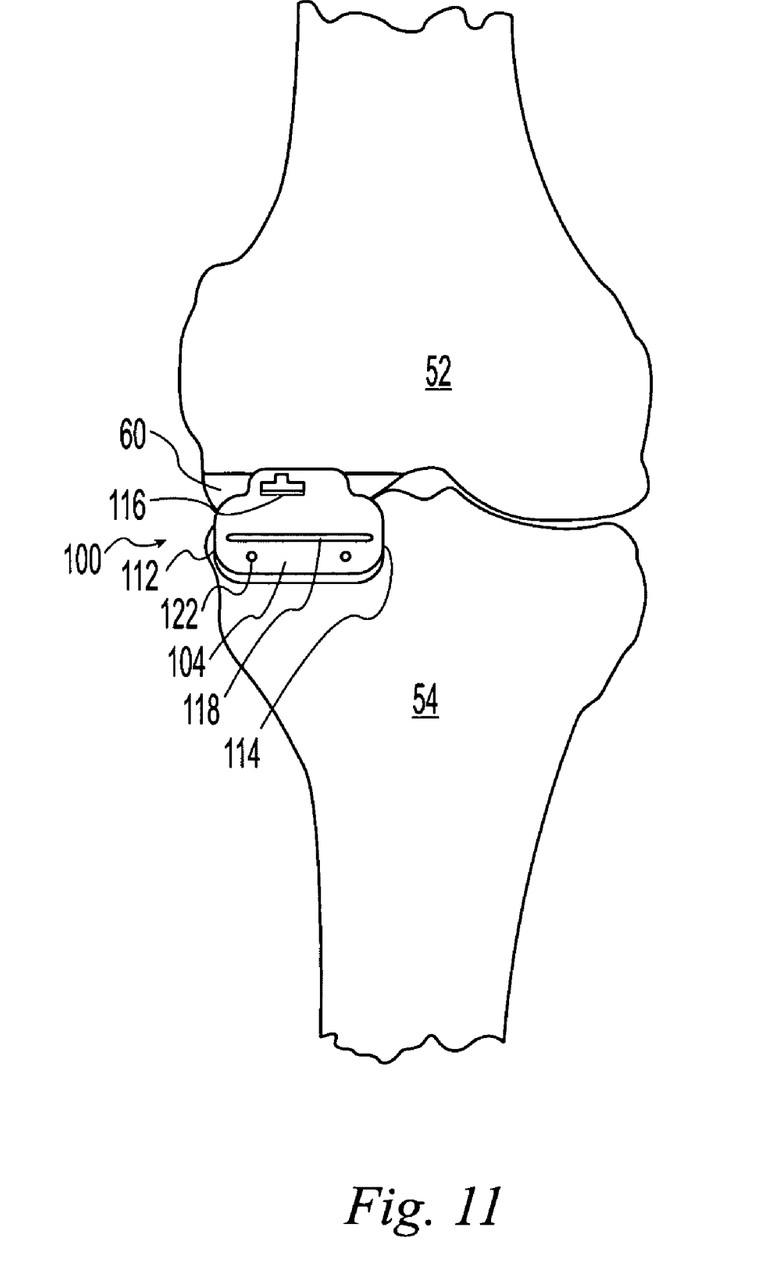
FIG. 11 is a front elevation view of the knee joint, cut guide, and spacer of FIG. 10.

FIG. 4 illustrates a knee joint 50 defined by a distal femur 52 and a proximal tibia 54. The invention will be illustrated in use to perform a unicondylar knee surgery in which a single compartment of the knee is replaced including a portion of one femoral condyle and a portion of the proximal tibia 54. However, it is contemplated that instruments and methods according to the present invention may also be used in a total knee replacement in which both the medial and lateral portions of the knee are resurfaced. In FIG. 4 a distal portion 56 of the medial femoral condyle has been resected using conventional techniques such as guiding a saw blade to resect the portion 56 while the knee is in flexion. FIGS. 5-7 illustrate a spacer 60 according to the present invention positionable on the cut surface 58 of the distal femur 52 to temporarily replace the resected portion 56. The spacer permits the knee joint 50 to be articulated between flexion and extension to check the joint kinematics and adjust the soft tissue balancing and limb alignment. If adjustments are necessary, the surgeon can recut the femur, release soft tissues, and/or try different thickness spacers 60 until the desired kinematics are achieved. The spacer 60 includes a generally arcuate body 62 having a planar seating portion 64 for seating on the cut surface 58 of the bone and an arcuate condylar portion 66 arching away from the seating portion generally in the shape of an anatomic femoral condyle. In the illustrative spacer, the seating portion 64 engages the bone surface in a simple frictional engagement. The condylar portion 66 is curved both in the sagittal plane (FIG. 6) to match the anterior/posterior curvature of the femoral condyle and the frontal plane (FIG. 7) to match the medial/lateral curvature of the femoral condyle. The spacer 60 is provided in a variety of sizes and curvatures to permit selection of a spacer that best matches the patient's anatomy. As best seen in FIGS. 5 and 11, the spacer 60 blends with the distal femur 52 to provide an approximately gapless fit to the bone and smooth articulation of the joint. The spacer 60 has a condylar thickness 68 parallel to the mechanical axis 4 of the femur. The spacer 60 is provided in different condylar thicknesses 68 to permit selection of a spacer thickness 68 to replace the same thickness of bone 56 that was resected to restore pre-surgical kinematics or a different thickness 68 to correct a varus or valgus abnormality of the pre-surgical knee. FIG. 7 illustrates a universal spacer 60 that has a generic projected frontal shape allowing it to be used on both medial and lateral sides of the knee joint 50. FIGS. 8 and 9 illustrate optional spacers 60a and 60b having anatomical frontal shapes that may provide a better fit to the medial and lateral sides of the knee 50. The universal spacer 60 of FIG. 7 reduces the required inventory of spacers while the spacers 60a and 60b of FIGS. 8 and 9 improve the medial/lateral fit of the spacer to the bone.

The spacer 60 includes a cut guide support 70 formed as a "T"-shaped stem projecting anteriorly from the body 62. The support forms a predetermined posterior slope angle 72 with the seating portion 64 to position the cut guide 100 to cut the proximal tibia 54 at a desired posterior slope angle. The spacer 60 is provided in different versions with different posterior slope angles that vary from zero degrees to ten degrees. Preferably, a plurality of spacers 60 is provided with a few representative angles including three degrees, five degrees, and seven degrees of posterior slope.

The cut guide 100 includes a body 102 having a front surface 104, a back surface 106, a top 108, a bottom 110, and sidewalls 112, 114. A "T"-shaped aperture 116 extends through the body 102 from the front surface 104 to the back surface 106. The aperture 116 engages the support 70 and constrains the cut guide 100 to linear translational adjustment along the support 70 so that the cut guide 100 can be slipped onto the support 70 and slid along the support 70 until it abuts the proximal tibia 54. The engagement of the aperture 116 and support 70 maintain a fixed posterior slope angular relationship between the cut guide 100 and the seating portion 64 and a fixed varus/valgus angular relationship between the cut guide 100 and the seating portion 64. Typically, it is desirable to have the tibial and femoral cut planes oriented at the same varus/valgus angle relative to the knee to avoid femoral component edge loading during articulation of the reconstructed joint. The illustrative resection apparatus maintains parallel varus/valgus rotation by way of the rotationally keyed support 70 and aperture 116. The parallelism of the slot 118 and the cut distal femoral surface 58 of the illustrative resection apparatus can be seen in FIG. 11.

However, there may be surgical situations in which it is desirable to vary the varus/valgus angular relationship of the femoral and tibial cut planes. By providing an optional keyless support 70 and aperture 116 the tibial cut plane 120 may be angled in varus/valgus rotation relative to the seating surface 64 and thus relative to the cut distal femoral surface 58. For example, the support 70 and aperture 116 may be circular to allow varus/valgus rotation about the support 70 axis.

Figure 10:
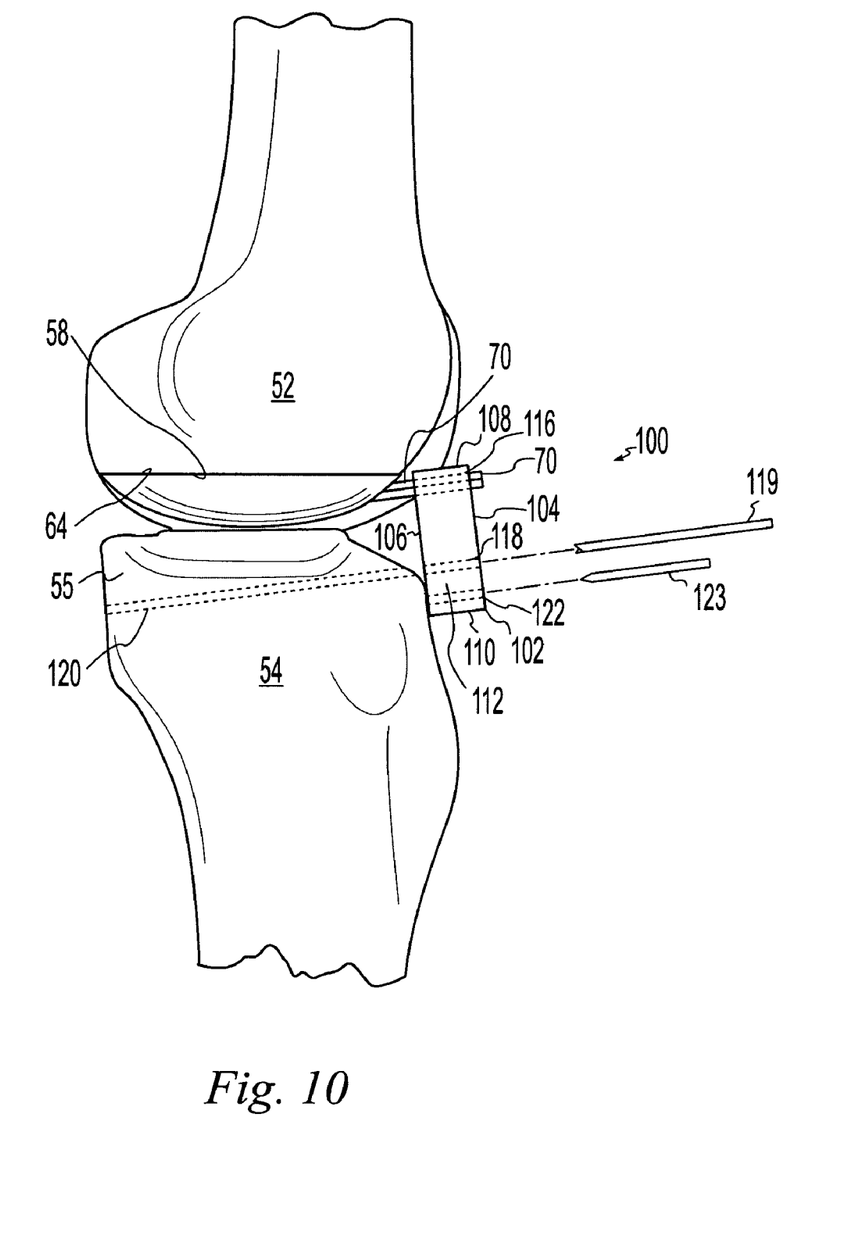
FIG. 10 is a side elevation view of the knee joint of FIG. 4 showing a cut guide in use with the spacer of FIG. 5.

A saw slot 118 extends through the body 102 from the front surface to the back surface 106. The saw slot 118 defines a cut plane 120 (FIG. 10) and guides a saw blade 119 within the cut plane to form a planar surface on the proximal tibia 54. The cut plane 120 is oriented parallel to the aperture 116 such that adjustment of the cut guide 100 along the support 70 does not change the cut plane location on the proximal tibia 54. Fixation holes 122 are formed through the body 102 from the front surface 104 to the back surface 106 to receive fixation pins 123 to maintain the cut guide's 100 position on the proximal tibia 54. The fixation holes 122 are oriented parallel to the cut plane 120 and aperture 116 so that the cut guide 100 may be removed from the support 70 and fixation pins 123 and then replaced on the fixation pins 123 during surgery if desired by the surgeon. For example, after establishing the cut guide 100 position, the surgeon may desire to remove the spacer 60 and/or reposition the knee before making the tibial cut. With the fixation pin holes 122 parallel to the support aperture 116, the cut guide 100 may easily be slid off of the pins 123 and support 70 and subsequently replaced on the pins 123 in the same position.

In knee replacement surgery, an incision is made to expose a portion of the knee. The illustrative unicondylar implants and instruments are suitable for a minimally invasive approach to the knee in which the incision is minimized to reduce trauma to the patient and speed recovery from the surgery. In particular, the simple, streamlined design of the spacers 60 and cut guides 100 permits them to be positioned through narrow incisions. The support 70 also is convenient as a handle for manipulating the spacers into and out of the incision. In an illustrative procedure, the knee 50 is flexed to approximately ninety degrees of flexion (FIG. 4) and a portion 56 of the distal femur 52 is resected. The resection is oriented so that the cut surface 58 of the distal femur 52 is perpendicular to the mechanical axis of the 4 of the femur 1. A spacer 60 is chosen that fits the cut surface 58 of the distal femur 52 and is positioned with the support 70 facing anteriorly (FIG. 5). The knee 50 is articulated through its range of motion with the tibia bearing on the condylar surface 66 of the spacer 60 while the surgeon assesses the limb alignment and soft tissue balancing. If adjustments are necessary, the surgeon may recut the femur, release soft tissues, and/or try a different thickness of spacer. When the surgeon is satisfied with the knee 50 kinematics, he returns the knee 50 to full extension and slides a cut guide 100 onto the support 70 (FIG. 10) until the back surface 106 of the cut guide 100 abuts the proximal tibia 54. The angle of the support 70 relative to the seating portion 64 establishes the posterior slope of the proximal tibia 54 relative to the mechanical axis of the femur. With the knee 50 in full extension, the saw slot 118 defines a cut plane 120 corresponding to the desired posterior slope angle. The cut guide 100 is fixed to the tibia by inserting pins through the fixation holes 122 and into the proximal tibia 54. With the cut guide 100 fixed to the proximal tibia 54, a saw blade 119 is guided through the saw slot 118 to resect a portion 55 of the proximal tibia in the cut plane 120. Optionally, the cut guide 100 can be removed from the fixation pins before the tibial resection is performed to permit the spacer 60 to be removed and/or the knee to be repositioned into a more convenient or safer position for the cut. The cut guide 100 can then be replaced over the pins to restore the desired orientation of the cut guide 100 and the resection performed. Additional femoral bone cuts are made as necessary to finish the femur to receive the femoral implant.

Figure 12:
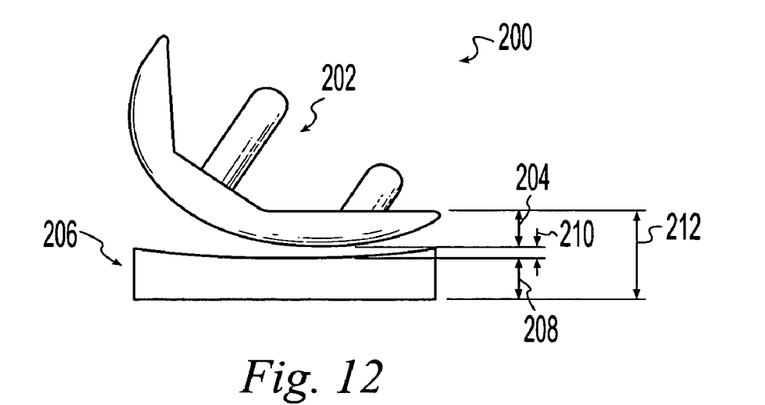
FIG. 12 is a side elevation view of a unicondylar knee implant.

An illustrative implant 200 is shown in FIG. 12. The implant 200 includes a femoral component 202 having a femoral component thickness 204 and a tibial component 206 having a tibial component thickness 208. The components 202, 206 are shown spaced apart a small amount corresponding to a desired joint laxity 210. A smaller spacing results in a tighter knee and a larger spacing results in a looser knee. The total of the femoral component thickness 204, the tibial component thickness 208, and the joint laxity 210 is represented by an overall implant thickness 212.

Figure 13:
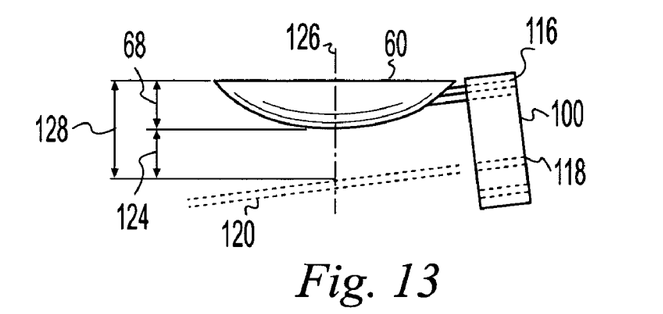
FIG. 13 is a side elevation view of the cut guide and spacer of FIG. 10.
Figure 14:
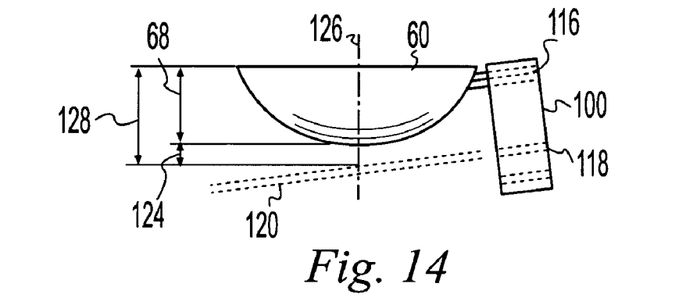
FIG. 14 is a side elevation view of the cut guide of FIG. 10 shown in use with a thicker spacer.
Figure 15:
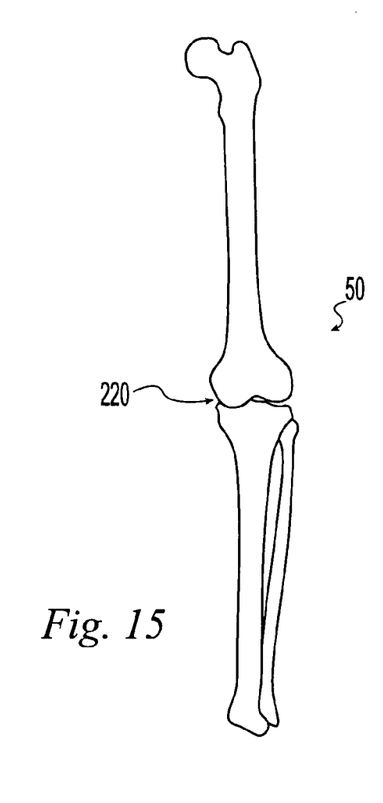
FIG. 15 is a front elevation view of a tibia and femur showing a varus knee joint.
Figure 16:
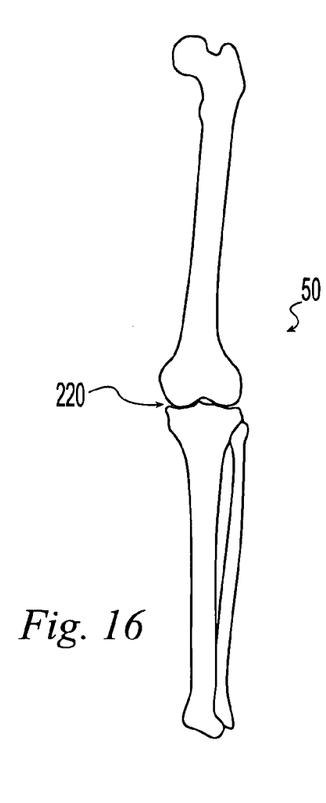
FIG. 16 is a front elevation view of a tibia and femur showing a normal knee joint.
Figure 17:
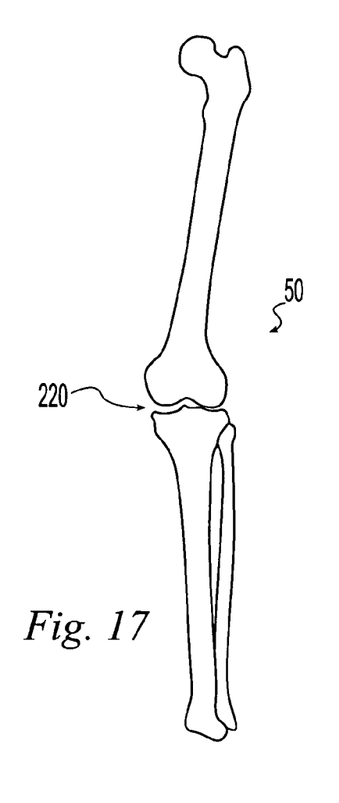
FIG. 17 is a front elevation view of a tibia and femur showing a valgus knee joint.

As seen in FIGS. 13 and 14, the thickness 68 of the spacer 60 and the relationship of the saw slot 118 to the support aperture 116 determines the depth of the tibial cut 124. The cut depth 124 is shown being measured at approximately one-half the anterior/posterior distance of the tibial plateau as indicated by the centerline 126. The distance 128 from the seating portion 64 to the cut plane 120 corresponds to the overall implant thickness 212. For surgery on a knee with normal pre-surgical limb alignment (FIG. 16), the spacer thickness 68 is chosen to correspond to the femoral component thickness 204 plus the desired joint laxity 210. This is evaluated during the articulation and adjustment discussed relative to FIG. 5. The resulting tibial cut depth 124 will then correspond to the tibial component thickness 208 and the post-surgical limb alignment will match the pre-surgical alignment. However, for correction of a varus knee (FIG. 15), the spacer thickness 68 is chosen to correct the limb alignment and will be different from the femoral component thickness 204. For unicondylar replacement of the medial compartment, increasing the bone spacing on the medial side 220 of the knee 50 will correct the limb alignment. Thus, inserting a thicker spacer 60 during the articulation and adjustment step (FIG. 5) of the operation will correct the alignment. During the tibial resection step of the surgery, the increased spacer 60 thickness 68 decreases the tibial cut depth 124 as seen in FIG. 14. When the implant components are inserted into the prepared knee, the tibial component will be positioned higher and thus the joint line 8 on the medial side of the knee 50 is raised and the varus deformity is corrected. For a valgus deformity (FIG. 17), a thinner spacer can be used to increase the tibial cut depth 124 and lower the joint line 8 on the medial side of the knee 50.

Although examples of a bone resection apparatus and its use have been described and illustrated in detail, it is to be understood that the same is intended by way of illustration and example only and is not to be taken by way of limitation. The invention has been illustrated in the context of a spacer and resection guide for spacing and resecting the medial side of the tibial plateau during unicondylar knee replacement surgery. However, the bone resection apparatus may be configured in other shapes and for use at other locations within a patient's body. Accordingly, variations in and modifications to the bone resection apparatus and its use will be apparent to those of ordinary skill in the art, and the following claims are intended to cover all such modifications and equivalents.

What is claimed is:

1. An apparatus for guiding a bone cut during knee joint replacement surgery in which a portion of the distal femur and a portion of the proximal tibia are removed and replaced with prosthetic components, the knee joint comprising a tibia and a femur and having a medial/lateral axis, an anterior/posterior axis, and a proximal/distal axis, rotation about the medial/lateral axis corresponding to posterior slope rotation, and rotation about the anterior/posterior axis corresponding to varus/valgus rotation, the apparatus comprising:

a spacer having a first surface engageable with the cut distal femoral bone, the first surface being substantially planar, a second surface opposite the first surface engageable with the uncut proximal tibial bone in joint articulating relationship, and a cut guide support, the cut guide support forming a predetermined posterior slope angle relative to the first surface, the posterior slope angle being greater than zero; and a tibial cut guide having a cutter guide defining a cut plane and a support engaging element engageable with the cut guide support, the cut guide support and support engaging element cooperating to position the cut plane at the predetermined posterior slope angle, wherein the cut guide support comprises an elongated member having a longitudinal axis and projecting outwardly from the spacer and wherein the longitudinal axis of the cut guide support forms the predetermined tibial posterior slope angle relative to the first surface.

2. The apparatus of claim 1 wherein the first surface comprises a planar seating portion.

3. The apparatus of claim 2 wherein the second surface comprises an arcuate condylar surface arching away from the planar seating portion generally in the shape of an anatomic femoral condyle.

4. The apparatus of claim 3 wherein the condylar surface is curved in a sagittal plane to match the general anterior/posterior curvature of an anatomic femoral condyle.

5. The apparatus of claim 4 wherein the condylar portion is curved in a frontal plane to match the general medial/lateral curvature of an anatomic femoral condyle.

6. The apparatus of claim 4 further comprising a plurality of spacers having different curvatures to permit selection of a spacer that best matches a patient's anatomy.

7. The apparatus of claim 3 wherein the spacer has a condylar thickness, the apparatus further comprising a plurality of spacers having different condylar thicknesses.

8. The apparatus of claim 1 wherein the apparatus further comprises a plurality of spacers having different posterior slope angles between three and ten degrees.

9. The apparatus of claim 1 wherein cut guide support comprises a non-circular cross section and the tibial cut guide comprises a body having a front surface, a back surface, and an aperture through the body from the front surface to the back surface, the aperture having a non-circular cross section for receiving the support, the aperture and support permitting linear translation of the cut guide relative to the spacer and maintaining a fixed angular relationship between the cut guide and the spacer.

10. The apparatus of claim 9 wherein the body further includes a saw slot extending through the body from the front surface to the back surface, the saw slot defining a cut plane, the cut plane being oriented parallel to the longitudinal axis of the support.

11. The apparatus of claim 10 wherein the body further includes at least one fixation hole formed through the body from the front surface to the back surface, the at least one fixation hole having a longitudinal axis, the at least one fixation hole being oriented such that its longitudinal axis is parallel to the longitudinal axis of the support.

12. The apparatus of claim 1 wherein cut guide support comprises a circular cross section and the tibial cut guide comprises a body having a front surface, a back surface, and an aperture through the body from the front surface to the back surface, the aperture having a circular cross section for receiving the support, the aperture and support permitting linear translation of the cut guide relative to the spacer, varus/valgus rotation of the cut guide relative to the spacer, and maintaining a fixed posterior slope angular relationship between the cut guide and the spacer.

13. A combination comprising an implant and an apparatus for guiding a bone cut during knee joint replacement surgery in which a portion of the distal femur and a portion of the proximal tibia are removed and replaced with prosthetic components, the knee joint comprising a tibia and a femur and having a medial/lateral axis, an anterior/posterior axis, and a proximal/distal axis, rotation about the medial/lateral axis corresponding to posterior slope rotation, and rotation about the anterior/posterior axis corresponding to varus/valgus rotation, the combination comprising:

an implant including a femoral component having a femoral component thickness and a tibial component having a tibial component thickness, the implant having an overall implant thickness which is the sum of the femoral component thickness, the tibial component thickness, and an additional joint laxity distance corresponding to a desired amount of joint laxity;

an apparatus, comprising:

a spacer having a first surface engageable with the cut distal femoral bone, the first surface being substantially planar, a second surface opposite the first surface engageable with the uncut proximal tibial bone in joint articulating relationship, and a cut guide support, the cut guide support forming a predetermined posterior slope angle relative to the first surface, the posterior slope angle being greater than zero; and a tibial cut guide having a cutter guide defining a cut plane and a support engaging element engageable with the cut guide support, the cut guide support and support engaging element cooperating to position the cut plane at the predetermined posterior slope angle, wherein the spacer further comprises a spacer thickness normal to the first surface and wherein the cut plane of the tibial cut guide is oriented parallel to the support engaging element, the cut plane being spaced a predetermined distance from the support engaging element such that with the support engaging element engaged with the cut guide support the cut plane is spaced from the second surface of the spacer by a tibial resection distance.

14. The combination of claim 13 further comprising a plurality of spacers, each of the plurality of spacers having a different spacer thickness, each spacer being engageable with the cut guide to produce a different tibial resection distance.

15. The combination of claim 13 wherein with the support engaging element engaged with the cut guide support the cut plane is spaced from the first surface a distance equal to the overall implant thickness.

* * * * *